United States Patent [19]
Pippert

[11] Patent Number: 5,256,371
[45] Date of Patent: Oct. 26, 1993

[54] METHOD AND ARRANGEMENT FOR DISINFECTING A DIALYSIS FLUID CIRCUIT

[75] Inventor: Manfred Pippert, Glashütten, Fed. Rep. of Germany

[73] Assignee: Medical Support GmbH, Rodgau, Fed. Rep. of Germany

[21] Appl. No.: 856,684

[22] Filed: Mar. 24, 1992

Related U.S. Application Data

[63] Continuation-in-part of Ser. No. 626,745, Dec. 13, 1990, abandoned.

[30] Foreign Application Priority Data

Dec. 13, 1989 [DE] Fed. Rep. of Germany ....... 3941103

[51] Int. Cl.⁵ .......................... A61L 2/00; B01D 63/00
[52] U.S. Cl. .................... 422/28; 134/104.1; 210/140; 210/321.69; 210/636; 422/2; 422/116; 422/117
[58] Field of Search ................. 422/28, 2, 3, 116, 117, 422/292; 134/58 R, 104.1, 166 C; 210/140, 321.69, 636

[56] References Cited

U.S. PATENT DOCUMENTS

| | | | |
|---|---|---|---|
| 4,166,031 | 9/1979 | Hardy | 210/140 |
| 4,834,888 | 5/1989 | Polaschegg | 210/321.69 |
| 4,908,188 | 3/1990 | Jeffris, III et al. | 422/116 |
| 5,147,613 | 9/1992 | Heilmann et al. | 422/116 |

*Primary Examiner*—Robert J. Warden
*Assistant Examiner*—L. M. Crawford
*Attorney, Agent, or Firm*—Juettner Pyle & Lloyd

[57] ABSTRACT

Not only the dialysis machine, but also its outer supply conduits and connection tubes together with the associated water distribution system can be flushed and disinfected in the present disinfection method by including these members in the cleaning circuit. Energy is saved and the amount of disinfectants is reduced during hot cleaning and chemical disinfection in a recirculatory process, and the duration of the disinfecting operations can moreover be decreased. Furthermore, a five-valve assembly is provided in or on the dialysis apparatus, in an additional apparatus with respect to the dialysis apparatus or in a water supply system integrated into the wall of a dialysis station for the dialysis apparatus so as to carry out the disinfection method, and a supply means is provided for introducing the disinfectant into the recirculatory circuit.

9 Claims, 7 Drawing Sheets

METHOD AND ARRANGEMENT FOR DISINFECTING A DIALYSIS FLUID CIRCUIT

CROSS REFERENCE

This is a continuation-in-part of application, Ser. No. 07/626,745, filed Dec. 13, 1990, now abandoned.

BACKGROUND OF THE INVENTION

This invention relates to a method of disinfecting a dialysis fluid circuit and also to an assembly for carrying out hygienic operations on a dialysis apparatus including a water supply and flushing circuit for a dialysis apparatus.

A dialysis fluid circuit is subject to many possible contamination sources, including the connection conduits of the dialysis apparatus, as well as the suction members and screw connections, the osmosis water and the mixture of fresh dialysis fluid with used dialysis fluid. Three disinfection methods have so far been used for killing bacteria and viruses that are nowadays known in dialysis. These methods are hot cleaning, autoclaving and chemical disinfection.

Use of these known methods involve only a partial disinfection of the machine. This means that although the dialysis apparatus or machine is disinfected, the distribution system thereof remains unsterile, so that at the beginning of the dialysis operation the disinfected machine may again be contaminated by unsterile connection conduits and suction members.

More specifically, the water inlet opening and the water outlet opening of a conventional dialysis apparatus are connected by means of connection conduits to the two wall connections of the fresh water inlet conduit and the water outlet conduit. These connection conduits are normally flexible tubes having a length of one or two meters. It is not possible to disinfect these tubes in known dialysis apparatus or in conventional disinfection methods. As a result, germs may collect in these connection conduits and again contaminate the apparatus at the beginning of a dialysis operation after the dialysis apparatus proper has been disinfected. In addition, it has not been possible to disinfect the wall connections of the inlet and outlet conduits in an adequate way, which will be explained in more detail hereafter.

As is generally known, the conduits which are installed in the wall, i.e. the fresh water inlet conduit and the water outlet conduit, must also be disinfected to dialysis stations at regular intervals so as to inactivate or flush away germs exiting in this area. This has so far been accomplished by flushing fresh water or a disinfectant through the fresh water supply conduit and the water outlet conduit, with the two wall connections (inlet and outlet) that are assigned to a respective dialysis apparatus being not included in this disinfection operation, as fluid cannot be flushed through said wall connections.

Other disadvantages of the known methods must be seen in the great thermal stress on the components during autoclaving. This might also be one of the reasons for the frequently occurring early failures of the components in the hydraulic circuit. Furthermore, contamination of the osmosis water may be due to the automatic forced flushing after chemical disinfection. Other disadvantages are the considerable amount of energy which is required for flow heating during hot cleaning and the great expenditure of time required by disinfecting operations between two dialysis treatments.

An object of the present invention is to provide a disinfection method of the above-mentioned type in which the whole dialysis fluid circuit, including the fresh water inlet conduit and the water outlet conduit which are located outside the dialysis apparatus, can be efficiently disinfected, so that renewed contamination of the dialysis apparatus at the beginning of the dialysis operation is prevented. Furthermore, the power consumption of the disinfection method may be reduced in comparison with conventional methods.

Another object of this invention is to provide an apparatus which is used in addition to a dialysis apparatus for carrying out hygienic operations and with which the disinfection method becomes feasible. Furthermore, in cases of application where the disinfection method includes chemical disinfection, a supply means may be provided with the metered supply of a chemical disinfection liquid.

In the method of the invention, five valves are provided, namely, a prevalve and a spaced-apart aftervalve in the water inlet conduit and the water outlet conduit, respectively, as well as a transverse connection valve disposed in a transverse connection conduit for connecting the inlet conduit to the outlet conduit between the pairs of valves. This valve assembly may be arranged on the dialysis apparatus, with the two prevalves being connected by means of tube conduits to the wall connections of the dialysis station. In the alternative, the valve may be accommodated in an additional apparatus which is directly arranged on the wall connections. In this case, the two aftervalves are connected through the tube conduits to the associated inputs of the dialysis apparatus.

In the method of the invention, the outer water circuit is first closed and flushed with fresh water before each dialysis treatment and before each program change in the dialysis apparatus in order to flush away any type of contamination and germ, which have collected in the outer connections, without these being capable of passing to the dialysis apparatus. To this end, the two aftervalves of the five-valve assembly are closed and the two prevalves as well at the transverse connection valve are opened in a first step, so that the interior of the dialysis apparatus is separated from the outer circuit for flushing with fresh water. In the subsequent second step, the aftervalves are opened and the transverse connection valve is closed, whereupon fresh water is flushed through the outer conduits and through the dialysis apparatus and its inner conduits. Subsequently, the prevalves are closed and the transverse connection valve is opened, whereby an inner circuit is formed which either comprises only the dialysis apparatus proper with the transverse connection conduit or also, in case the five-valve assembly is accommodated in an additional apparatus, the tube conduits leading to the additional apparatus. The heating source and the pump of the dialysis apparatus are now switched on, so that the inner circuit can be subjected to hot cleaning in the recirculatory process.

The last step of the disinfection method of the invention may be followed by a dialysis treatment. Instead of this, the apparatus may also be switched off. If a dialysis treatment is carried out at a later time, the outer circuit will again be flushed with fresh water.

In the method of the invention all components of the dialysis fluid circuit, including the outer water connection conduits, are subjected to a disinfecting or cleaning operation, so that neither the disinfected dialysis apparatus nor the water connection conduits thereof will cause any contamination of the dialysis fluid. Moreover, since the hot cleaning step is carried out in a recirculatory process, the energy consumption is thereby reduced to a considerable degree, as the water heated by the heating element of the dialysis apparatus is not immediately discharged after its passage through the dialysis fluid circuit, but circulated during the entire hot-cleaning process. Apart from the dialysis apparatus, all connection conduits and their screw connections or the like are efficiently disinfected if the five-valve assembly is accommodated in an additional apparatus to be provided on the wall connections.

If the disinfection method of the invention is to include chemical disinfection, the prevalves are closed in accordance with the invention subsequent to the flushing of the dialysis fluid circuit with fresh water, whereas the transverse connection valve is opened, a supply means containing a specific amount of liquid chemical disinfectant is connected to two associated inlets of the dialysis apparatus, and the disinfection suction pump of the dialysis apparatus is subsequently operated for a specific period of time, whereby the chemical disinfectant is passed from the supply means into the dialysis fluid circuit and a chemical disinfection operation takes place in recirculation. On completion of this process the connection conduits and the dialysis apparatus are flushed to free them from the chemical disinfectant after the pump has been put out of operation, the transverse connection valve has been closed and the prevalves have been opened. Thereafter, the previously described hot cleaning process takes place.

During chemical disinfection the two connection conduits or tubes and their fittings are thus efficiently disinfected or flushed as well. Since this process is also carried out in recirculation, the necessary amount of disinfectant is thus considerably reduced in comparison with the quantities required in conventional methods. As a result, the method of the invention is safer from an environmental point of view and less damaging to the components of the apparatus.

The duration of the disinfecting operations can be decreased on account of the increased efficiency and temperature resulting from the recirculatory process. As a consequence of this, the standstill times are reduced. Furthermore, the disinfection method of the invention helps to same osmosis water and is less stressful to the components of the dialysis fluid circuit, so that the parts thereof have a longer service life.

The apparatus of the invention which is used in addition to the dialysis apparatus comprises a fresh water inlet conduit portion in a housing. This portion includes a connection for a fresh water inlet conduit in the wall of a building and a prevalve having arranged thereafter an intermediate conduit portion, an aftervalve and a connection for an inlet connection conduit of the dialysis apparatus. Also, a water outlet conduit portion is provided with a connection for a water outlet conduit in the wall of a building and with a prevalve followed by an intermediate conduit portion, an aftervalve and a connection for an outlet connection conduit of the dialysis apparatus. The intermediate connection portions are connected via a transverse connection conduit portion which is provided with a transverse connection valve. A valve switching means may be provided, which comprises a control conduit for each of the valves and is electrically connected to the dialysis apparatus by coupling, so that the valves can be switched on and off in accordance with given programs of the dialysis apparatus.

Hence, the disinfection method of the invention in which the aftervalves, the prevalves and the transverse connection valve are switched in accordance with the program of the dialysis apparatus is feasible on all types of dialysis apparatus.

The apparatus of the invention may also include an adjustable switch-on clock to allow the automatic start of a hygiene program.

A fail-safe circuit for the valves may be provided to assure that the individual steps of a hygiene program or a disinfection program are only taken if all valves are in their correct positions. To this end, the valves which act as feedback means may be provided with a small limit switch whose respective position is interrogated, so that e.g. a flushing program is only started if it is ensured that all valves are in their correct positions.

Furthermore, the apparatus of the invention includes a diagrammatic display of the valves which indicates, e.g. through light signals, which valves are opened or closed.

In accordance with another embodiment, the prevalves and the transverse connection valve together with their connection portions may also be part of a supply panel or supply rail provided in the wall of a building. In this embodiment, a water supply means has an inlet prevalve arranged in front of the formerly single inlet valve in the inlet conduit and an outlet prevalve is arranged in front of the outlet valve in the outlet conduit (both of the prevalves being disposed at the side facing away from the dialysis apparatus) and the two conduit portions between the series-arranged valves are connected to a transverse connection conduit comprising a transverse connection valve. In this case, all valves are preferably actuable by an automatic actuation means, preferably in an electromagnetic way, in order to be switchable by the program of the connected dialysis apparatus. Corresponding electric circuits and connections are of course provided in this case.

The five-valve assembly which has been described above in connection with the additional apparatus may also be provided directly on or in a dialysis apparatus, i.e., the fresh water inlet conduit of the apparatus includes a pair of valves consisting of a prevalve and an aftervalve that are spaced apart, with a corresponding pair being provided in the water outlet conduit of the apparatus. Hence, the transverse connection conduit with the transverse connection valve is also positioned on or in the dialysis apparatus. In this embodiment of the invention, which is also preferred, the two prevalves are connected through conduits, preferably through a flexible tubes, to the wall connections of a dialysis station.

The operation of this five-valve assembly that is integrated into the dialysis apparatus corresponds to that of the above-described additional apparatus. An outer water circuit which leads from the connection at the wall side via the fresh water supply conduit, the prevalve in the supply conduit of the apparatus, the transverse connection conduit and from there via the water outlet tube to the water discharge conduit at the wall side is formed by opening the two prevalves and the transverse connection valve and by closing the two aftervalves. Fresh water can be flushed through this outer circuit so that germs, harmful deposits, etc., are prevented from collecting, in the connections at the inlet side and the inlet tube, and cannot pass into the dialysis apparatus after the valves have been opened.

The flushing of the outer circuit free from contamination is also of great importance in cases where a separate osmosis device or reverse osmosis device is arranged in the inlet conduit upstream of the dialysis apparatus for decalcifying the fresh water supplied.

This reverse osmosis device must be disinfected from time to time. To this end, a disinfectant is introduced into the device. It has so far not been possible to flush out the disinfectant in the state in which the reverse osmosis device is connected to the inlet conduit, since in such a case the disinfectant would flow into the dialysis apparatus. This is why it has been necessary to remove the reverse osmosis device from the circuit and to disinfect it separately.

This is no longer necessary with the dialysis apparatus of the invention comprising the five-valve assembly because the disinfectant can be discharged by flushing via the outer circuit without entering the dialysis apparatus. As a result, the reverse osmosis device can be disinfected at a considerably faster rate and more easily.

The supply means of the invention for supplying two liquids, of which at least one is supplied in metered amounts, comprises a hollow cylinder containing a displacable piston in fluid-tight fashion. This piston defines front and rear cylinder chambers whose volume is variable by the movement of the piston. In the rear end portion the hollow cylinder includes a liquid entrance port through which water enters in the disinfection method of the invention, an in the front end portion it comprises a port through which a liquid can be filled into the front cylinder chamber. In the disinfection method of the invention this liquid is a chemical disinfectant. The front port also serves the discharge of both liquids. Moreover, a liquid passage means is provided to extend from the rear cylinder chamber to the front cylinder chamber which in a given, preferably extended position of the piston allows the discharge of the liquid contained in the rear cylinder chamber into the front cylinder chamber and out of the front port of the hollow cylinder.

In this embodiment, a predetermined amount of a chemical disinfectant is filled under pressure. preferably by means of an automatic filling means, through the front port into the front cylinder chamber. This port may be closable by a valve which, when under pressure, can perform opening operations in both directions.

In accordance with another embodiment, two connectors for securing the supply means to the dialysis apparatus are mounted preferably laterally on the supply means, with the liquid (water) being introduced through one of the connectors into the rear cylinder chamber. Furthermore, the invention provides for an electrical contact to be made by the engagement of the connectors, which contact effects the automatic adjustment of a disinfection program including chemical disinfection.

The liquid passage means between the rear and front cylinder chambers is preferably formed by a plurality of axial holes which cut away circumferential portions of the inner wall of the inner front end portion of the hollow cylinder from the outside through the front cylinder bottom. The cylinder bottom is subsequently closed by inserting, preferably gluing in place, cylindrical filling members that close the front cylinder bottom again. Hence, expansions on which the pressurized liquid contained in the rear cylinder chamber can flow around the piston, which is preferably sealed laterally by an O-ring, only remain in the front end portion of the inner cylinder wall.

To ensure that the front cylinder chamber of the supply means can always be refilled with a liquid without any additional operation being required therefor, a spring may be disposed between the front bottom of the hollow cylinder and the piston, preferably in the form of an axially extending helical spring, which is compressed when the piston is moved forward to the area of the liquid passage means, so that the resilient force presses the piston back again into a rear area in which the piston tightly rests on the inner cylinder wall when the piston is no longer acted upon by liquid pressure in the direction of forward movement. On completion of a chemical disinfection, the piston is thus automatically pressed back into a position in which the two cylinder chambers are separated from each other. As a result, the front chamber can again be filled with a liquid. Of course, this operation can be carried out with an automatic filling means or by hand.

DESCRIPTION OF THE PREFERRED EMBODIMENTS

Figure 1:
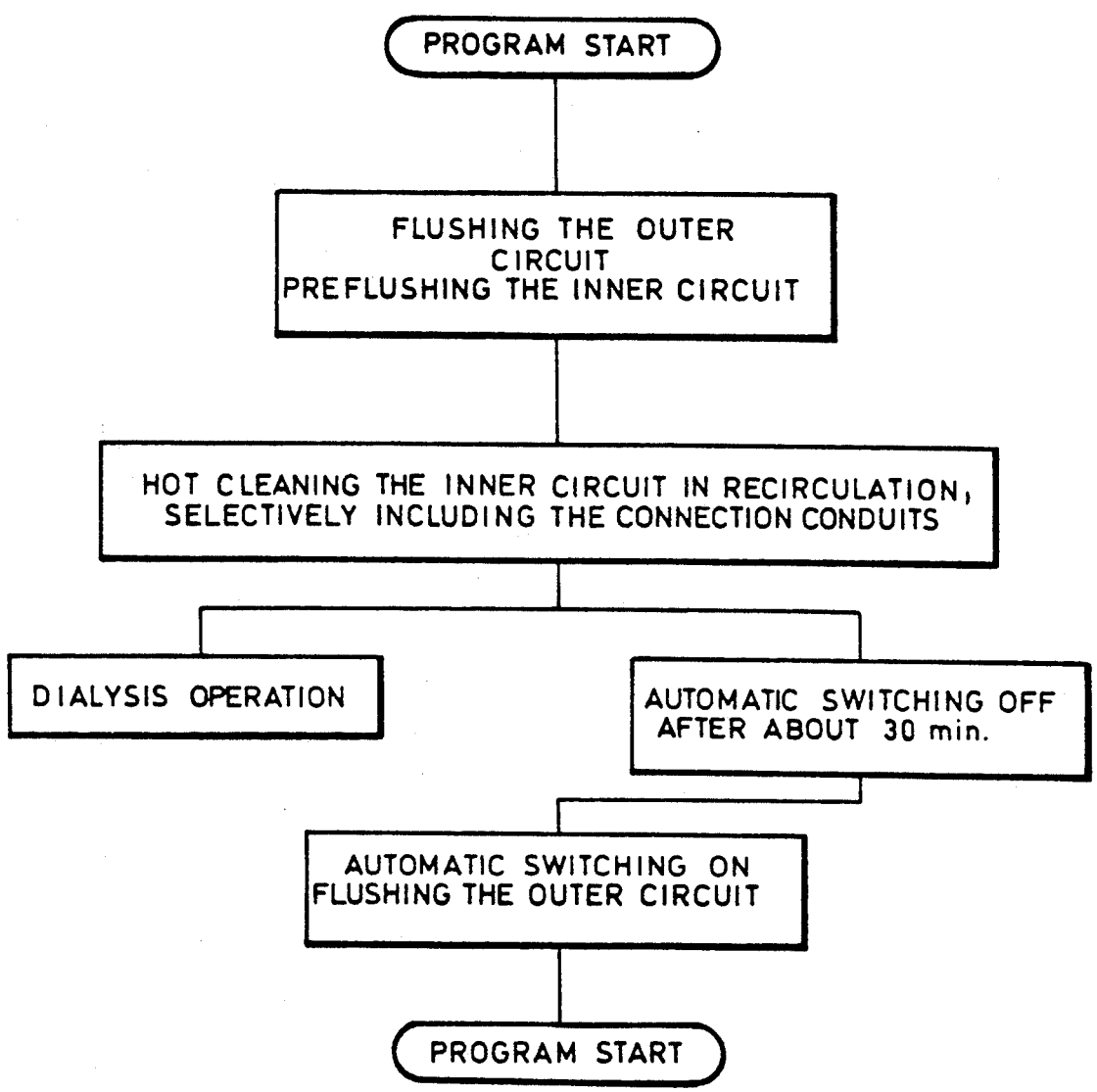
FIG. 1 shows a flow chart of a hot cleaning process of the invention for a dialysis fluid circuit.

FIG. 1 shows a flow chart of a hot cleaning process wherein the first step consists in flushing the outer circuit, and the subsequent second step in which the dialysis fluid circuit is flushed with fresh water in about three minutes, while the time interval of the subsequent hot cleaning step is preselectable. If a dialysis operation is not immediately carried out after the hot cleaning process, the subsequent flushing program can be preselected with the switch-on clock of the apparatus shown in FIG. 3 after the automatic switching off. The time interval of this flushing program is preselectable.

Figure 2:
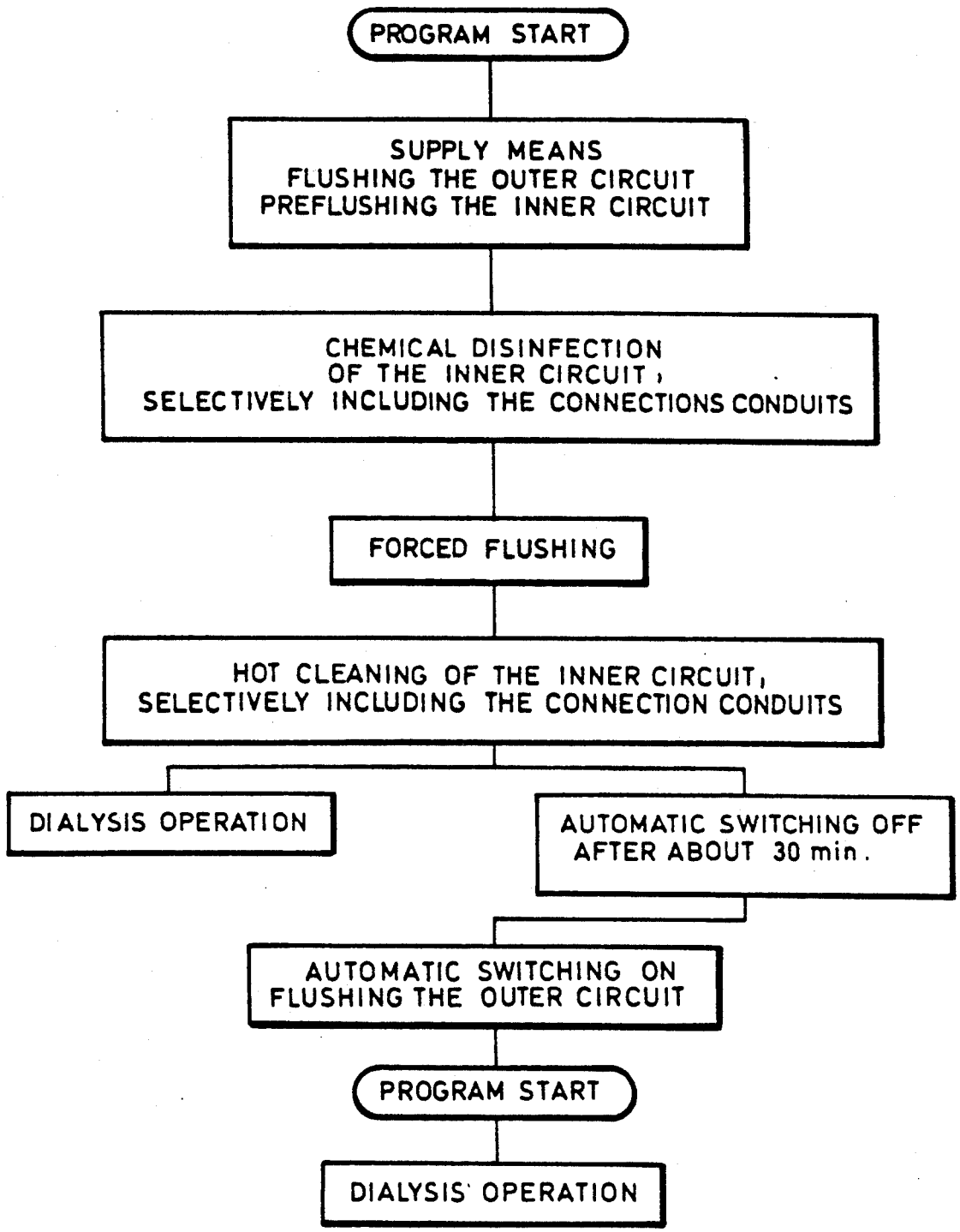
FIG. 2 shows a flow chart of a disinfection method of the invention, wherein chemical disinfection is combined with hot cleaning.
Figure 3:
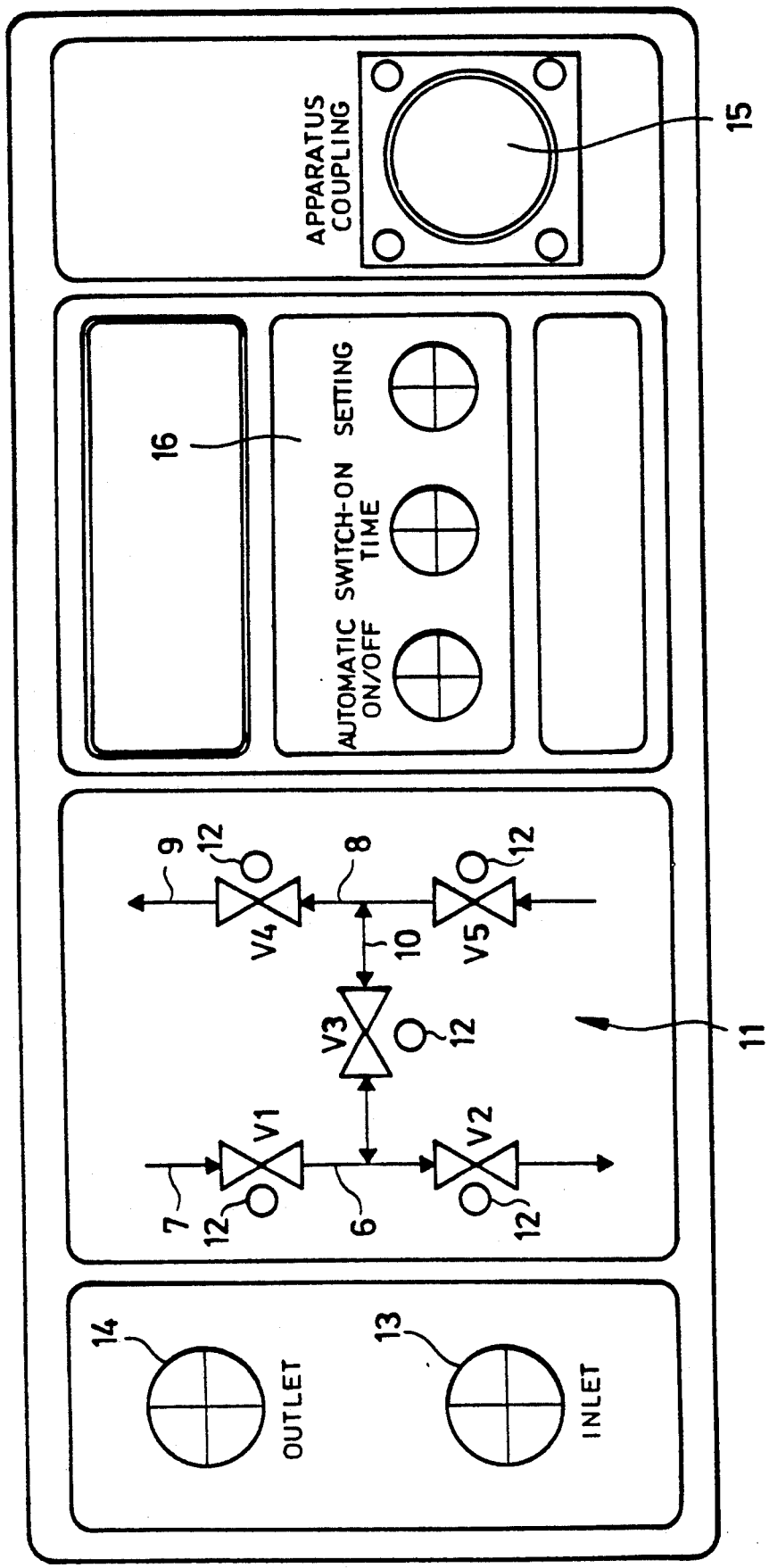
FIG. 3 shows an additional apparatus of the invention for carrying out hygienic operations on a dialysis apparatus.

In the combination program shown in FIG. 2, the outer circuit is first flushed, whereupon the dialysis apparatus together with the associated distribution system is flushed for three minutes. The chemical disinfection step whose duration was preselectable is then executed. To this end, the supply means is filled with 100 ml. of a disinfectant which if fed into the dialysis fluid circuit within three minutes. The individual steps of the method will moreover become apparent from the flow chart:

FIG. 3 which shows the apparatus for carrying out hygienic operation on a dialysis apparatus is diagrammatic view of the valve arrangement of the apparatus. This arrangement consists of a prevalve V1, an intermediate conduit portion 6 and an aftervalve V2 for the fresh water inlet conduit 7, a prevalve V4, an intermediate conduit portion 8 and aftervalve V5 of the water outlet conduit 9, and a transverse connection conduit V3 in a transverse connection conduit portion 10.

The diagrammatic representation 11 of this valve arrangement provided inside the apparatus may include a small signal lamp 12 for each of the valves for indicating the respective switching state of the valves.

Figure 4:
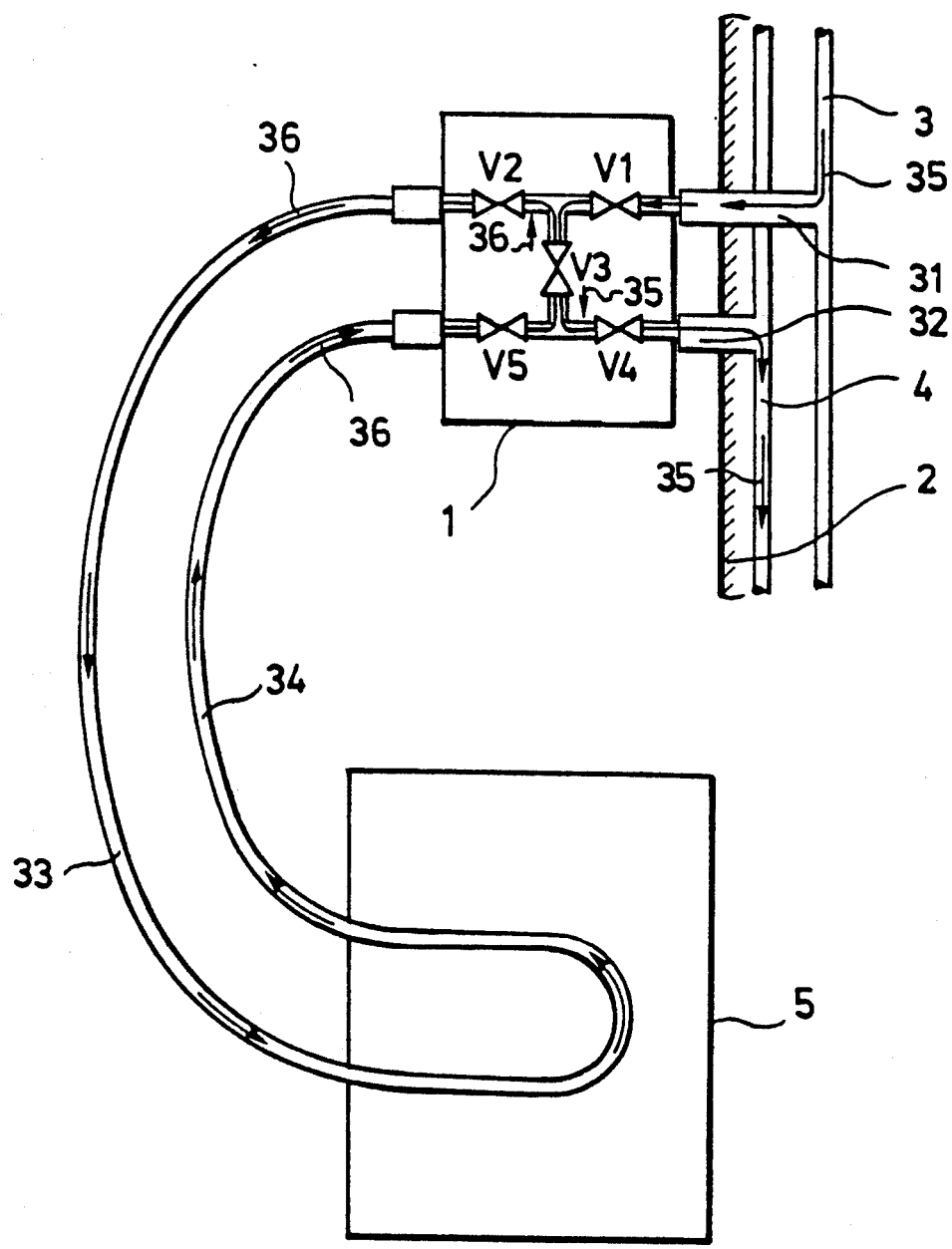
FIG. 4 is a diagrammatic layout showing an arrangement of a dialysis apparatus and an additional apparatus in the operative state in a dialysis station.

As shown in FIG. 4, prevalves V1 and V4 are connected to a fresh water inlet conduit 31 at the wall side and to water outlet conduit 32 at the wall side. For the connection of the dialysis apparatus to these water conduits, inlet 13 and outlet 14 are provided in the additional apparatus.

Furthermore, the apparatus includes a coupling 15 in the form of a jack plug for short-circuiting the dialysis apparatus to the valve switching means located in the additional apparatus, so that valves V1-V5 can be switched in accordance with the program of the dialysis apparatus. Furthermore, the additional apparatus illustrated in FIG. 3 comprises a switch-on clock or timer 16 with the aid of which the switch-on time of the desired programs is preselectable.

FIG. 4 is a substantially diagrammatic layout illustrating the arrangement of the additional apparatus 1 near a wall 2 of a dialysis station. Wall 2 is here provided with a fresh water inlet conduit 3 including a connection 31 and with a water outlet conduit including an associated connection 32. The corresponding conduit sections of the additional apparatus 1 are connected to connections 31 and 32.

The additional apparatus is connected via water outlet conduits 32 and 33 to corresponding connections of a dialysis machine 5.

An outer circuit is formed by closing valves V2 and V5 and by opening valves V1, V3 and V4 and also valves (not shown) which are positioned on connections 31 and 32. This outer circuit is outlined by arrows 35 and permits the flushing of the associated conduits, whereby germs, deposits, etc., can be flushed away by means of supplied fresh water into outlet conduit 4 without these substances being capable of passing into the dialysis apparatus.

An inner circuit which is outlined by arrows 36 and permits the disinfection of the dialysis apparatus, including tubes 32 and 33, and of the associated conduits in the additional apparatus 1 in a recirculatory process is formed by closing valves V1 and V4 and by opening valves V2, V3 and V5.

When the two disinfection circuits 35 and 36 are viewed together, it becomes apparent that an uninterrupted disinfection of the whole system is made possible by the present invention.

Figure 5:
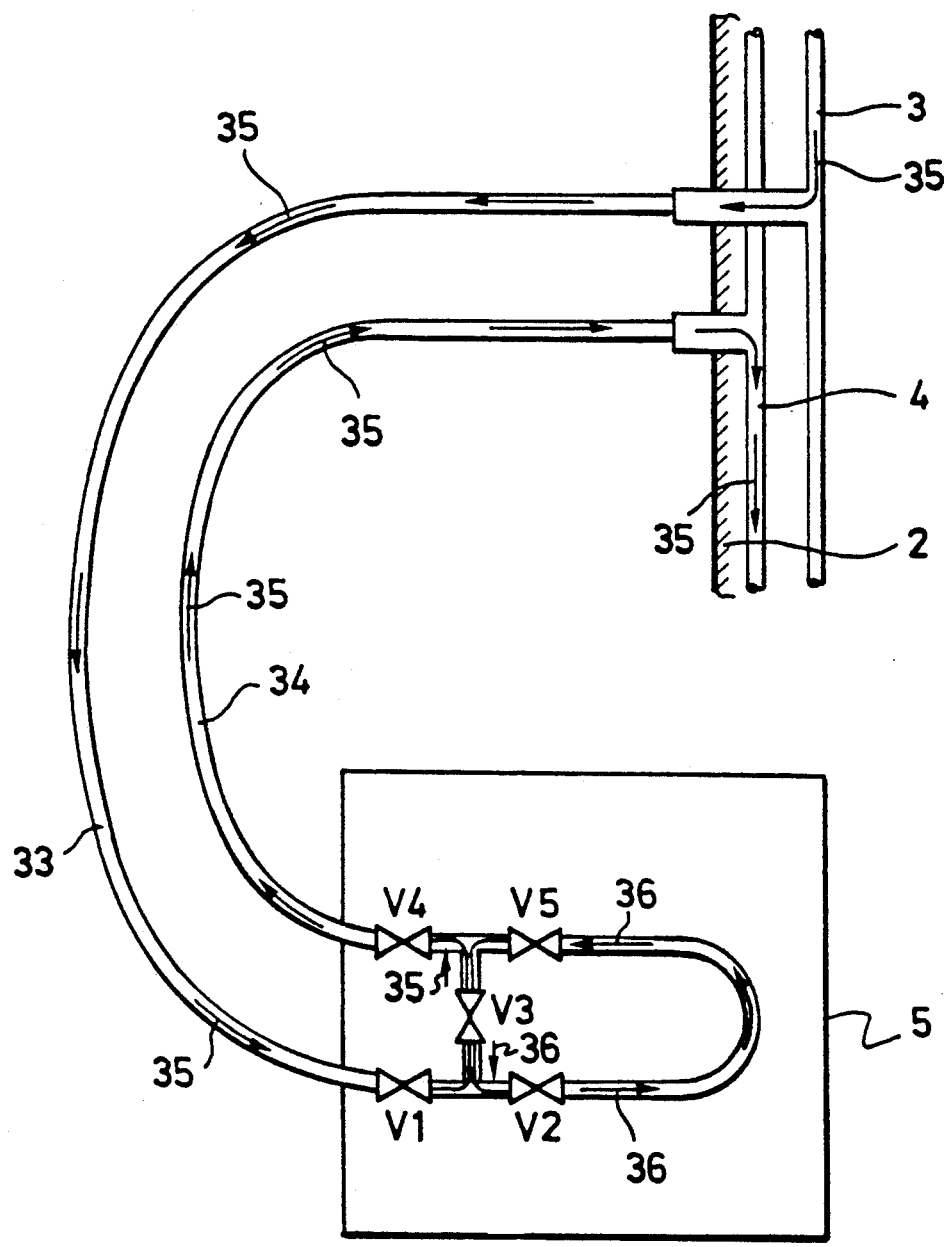
FIG. 5 is an arrangement similar to FIG. 4, with the five-valve assembly being provided in or on the dialysis apparatus.

FIG. 5 is just a diagram which illustrates the direct arrangement of the five valves V1-V5 in the dialysis machine. In this assembly, tubes 33 and 34 pertain to the outer circuit 6 which must be flushed with fresh water, and not the inner circuit which is disinfected in a recirculatory process.

Figure 6:
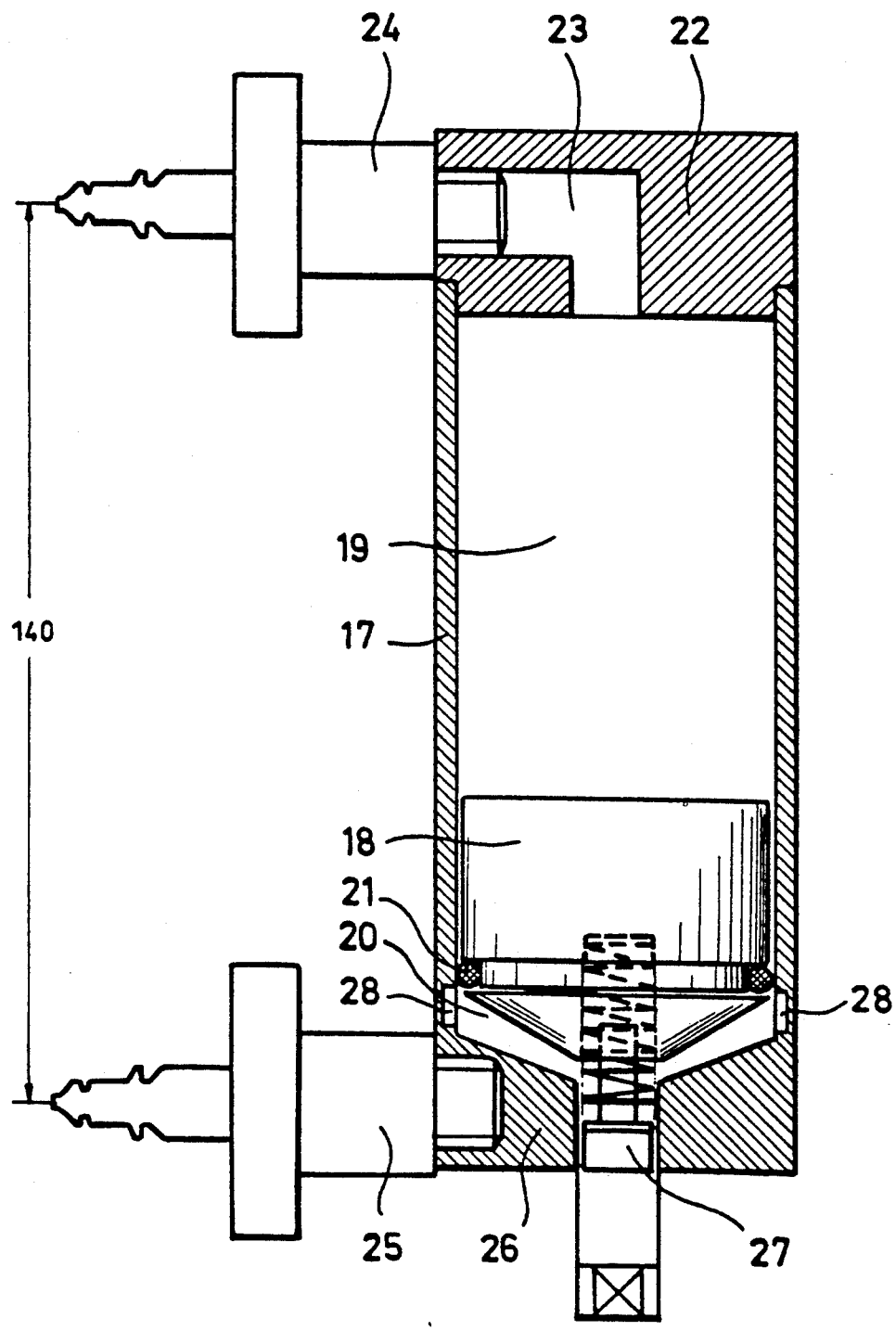
FIG. 6 is a longitudinal section through a supply means of the invention.

The supply means shown in FIG. 6 comprises a hollow cylinder 17 in which a piston 18 can be reciprocated so as to divide the inner chamber of hollow cylinder 17 into a rear cylinder chamber 19 and a front cylinder chamber 20. Piston 18 is sealed by means of an O-ring 21 of silicone relative to the inner wall of cylinder 17.

Cylinder bottom 22, which is the upper one in the figure is glued to the tubular wall of cylinder 17 and comprises an upper or rear entrance port 23 for a first liquid (water) which is supplied through an inserted connector 24 by means of which the supply means can be secured to a dialysis apparatus. To this end, another lateral connector 25 is provided at the other axial end. Connector 25 only serves fastening purposes and is not used for supplying liquid. Furthermore, the two connectors 24, 25 establish an electrical contact which signals to the dialysis apparatus that a chemical disinfection operation to be carried out.

The lower (front) cylinder bottom 26 has arranged therein a central front port 27 through which a second liquid, e.g. a liquid chemical disinfectant, can be introduced into the front cylinder chamber 20. Port 27 is closed by means of a valve which, when under pressure, can perform opening operations in both directions. Furthermore, front port 27 serves the discharge of the first liquid contained in the front cylinder chamber 20 and the discharge of the liquid in the real cylinder chamber 19 of this liquid can flow around piston 18.

For this purpose, a liquid passage means shaped in the form of a plurality of circular holes 28 is provided in the front (lower) end portion of the inner wall of hollow cylinder 17. If piston 18 is moved forward to such a degree that its sealing ring 21 is positioned in the area of the expansion created by holes 28, the liquid inside the rear cylinder chamber 19 can radially flow around sealing ring 21 at the outside and thus pass into the front cylinder chamber 20 from which it discharges the remaining liquid amount (disinfectant) and exits itself through port 27.

Figure 7:
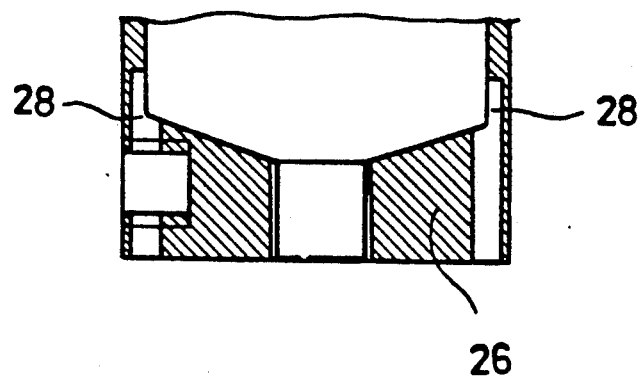
FIG. 7 shows the front cylinder bottom of the supply means illustrated in FIG. 6 after a first step has been taken for making the liquid passage means.

As becomes apparent from FIG. 7, the liquid passage means is constructed such that a plurality of cylindrical holes are formed from the end face. In the area of cylinder bottom 26 these holes are subsequently closed again by correspondingly formed filling members which are e.g. glued in place. Thereafter, the recesses shown in FIG. 6 will still remain in the inner cylinder wall.

Figure 8:
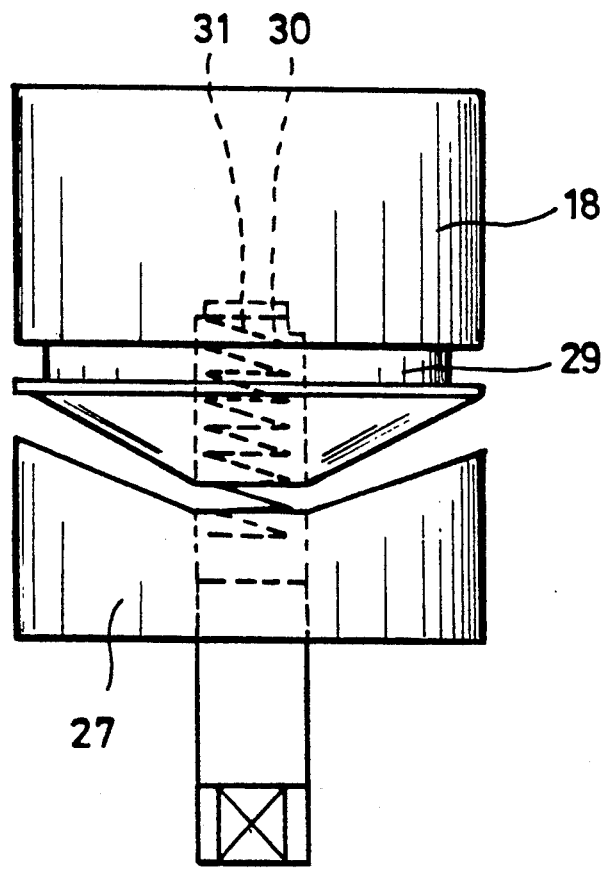
FIG. 8 shows the area of the piston of the supply means on an enlarged scale.

Piston 18 which is shown in FIG. 8 on an enlarged scale comprises an annular groove 29 for receiving O-ring 21 and a hole 30 for receiving helical spring 31 whose counterseat is formed by the valve of port 27. When the piston has reached such an extended position that its O-ring 21 is positioned in the area of expansions 28, helical spring 31 is compressed to such a degree that is automatically presses piston 18 back again, i.e. out of the area of expansions 28, if piston 18 is no longer acted upon by pressurized fluid. Hence, fluid-tight separation between the rear and front cylinder chambers 19, 20 is again obtained, so that the front chamber 20 can again be filled with a disinfectant without the latter flowing to the rear chamber 19.

As illustrated in FIGS. 6 and 8, the piston is shaped as a truncated cone at its (lower) front side, while cylinder bottom 26 is configured as an inversely truncated cone at its inner side. The angle of inclination of the piston is here greater than that of the cylinder bottom. This configuration facilitates the smooth and easy discharge of the liquid contained in the front cylinder chamber 20 and permits the liquid to flow out of the rear cylinder chamber.

The supply apparatus is not only suited for chemically disinfecting a dialysis apparatus, but quite generally for supplying two liquid or gaseous media, of which at least one is supplied in metered amounts. It is here not only possible to move the piston under overpressure into the rear cylinder chamber, but it is also possible to move it under vacuum into the front cylinder chamber (suction).

I claim:

1. An apparatus for flushing a dialysis machine having an inlet and an outlet and wherein water is provided from an an external water supply and is circulated through the machine and into a drain, said apparatus comprising:
   - a water inlet portion comprising a prevalve connected to an external water supply, an intermediate conduit connected to said prevalve, and an aftervalve connected to the intermediate conduit and to the inlet of a dialysis machine
   - a water outlet portion comprising a prevalve connected to a drain, an intermediate conduit connected to said prevalve, and an aftervalve connected to said intermediate conduit and to an the outlet of the dialysis machine
   - a transverse conduit connected between said intermediate conduits and a valve on said transverse conduit, and
   - means for opening and closing said valves in sequence to allow independent circulation of water through a first external circuit confined through said transverse conduit and prevalves to flush the prevalves, and circulation of water in a second circuit confined through said transverse conduit, aftervalves and dialysis machine.

2. The apparatus of claim 1 wherein said means for opening and closing said valves additionally comprises a switch-on timer to control the start of the flushing operation.

3. The apparatus of claim 1 additionally comprising a fail-safe circuit means to prevent operation of the apparatus in the event that any of the valves are in a faulty position.

4. A dialysis apparatus having an internal fluid flow circuit having an inlet and outlet and an external water supply having a water inlet conduit and water outlet conduit connected to the inlet and outlet of said apparatus, said apparatus comprising a pair of spaced on-off valves on each of a water inlet and water outlet conduits, a transverse conduit connected between the water inlet and water outlet conduits and between the respective pairs of valves, said valves being operable to provide a first outer circuit to circulate water from said water inlet conduit and outlet conduit through said transverse conduit, and a second circuit to circulate water through an internal fluid flow circuit of a dialysis apparatus.

5. The apparatus of claim 4 additionally comprising a timer for opening and closing said valves in a defined sequence.

6. The apparatus of claim 4 wherein said valves are opened and closed in a defined sequence, and fail-safe means is provided to prevent operation of said apparatus when a valve is opened or closed in faulty sequence.

7. A method for disinfecting a dialysis apparatus, wherein the apparatus comprises an internal liquid flow circuit having an inlet and an outlet, said method comprising:
   a. connecting an inlet and outlet of a dialysis apparatus, respectively to a water supply and a drain,
   b. providing first and second spaced shutoff valves in each of an inlet and outlet conduits, with the first shutoff valves being adjacent to the inlet and outlet of the apparatus, respectively,
   c. providing a transverse valve connecting the inlet and outlet conduit between the spaced first and second shutoff valves thereof,
   d. closing the first valves, and opening the second valves and the transverse valve to provide an external flow circuit, and flushing the external circuit and second valves with water,
   e. opening the first and second valves and closing the transverse valve to provide an internal flow circuit, and flushing the internal flow circuit of the apparatus with water, and
   f. closing the first valves and opening the transverse and second valves and circulating heated water in the internal flow circuit of said apparatus.

8. The method of claim 7 comprising an additional step, after the step of circulating heated water in the internal flow circuit of said apparatus, of passing a supply of disinfectant through the internal flow circuit of the apparatus.

9. The method of claim 8 comprising an additional step of flushing the internal flow circuit of said apparatus with water to remove the disinfectant.

* * * * *